US010426838B2

(12) United States Patent
Honda et al.

(10) Patent No.: US 10,426,838 B2
(45) Date of Patent: Oct. 1, 2019

(54) COMPOSITE PARTICLES INCLUDING CELLULOSE, INORGANIC COMPOUND, AND HYDROXYPROPYL CELLULOSE

(71) Applicant: ASAHI KASEI KABUSHIKI KAISHA, Tokyo (JP)

(72) Inventors: Yosuke Honda, Tokyo (JP); Kazuhiro Obae, Tokyo (JP); Hanayo Kodama, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/773,838

(22) PCT Filed: Nov. 22, 2016

(86) PCT No.: PCT/JP2016/084657
§ 371 (c)(1),
(2) Date: May 4, 2018

(87) PCT Pub. No.: WO2017/094569
PCT Pub. Date: Jun. 8, 2017

(65) Prior Publication Data
US 2018/0326063 A1 Nov. 15, 2018

(30) Foreign Application Priority Data
Nov. 30, 2015 (JP) ................. 2015-233138

(51) Int. Cl.
| A61K 47/02 | (2006.01) |
| A61K 47/38 | (2006.01) |
| C08J 3/12 | (2006.01) |
| C08K 3/00 | (2018.01) |
| C08K 3/22 | (2006.01) |
| C08K 3/34 | (2006.01) |
| C08L 1/02 | (2006.01) |

(Continued)

(52) U.S. Cl.
CPC .............. *A61K 47/02* (2013.01); *A23P 10/28* (2016.08); *A23P 30/10* (2016.08); *A61K 9/2009* (2013.01);
(Continued)

(58) Field of Classification Search
None
See application file for complete search history.

(56) References Cited

U.S. PATENT DOCUMENTS 6,117,451 A * 9/2000 Kumar ................. A61K 9/2009
424/464
2012/0232167 A1 9/2012 Takeuchi et al.
2013/0108872 A1 5/2013 Magome et al.

FOREIGN PATENT DOCUMENTS

EP 2589618 A 5/2013
GB 1324191 A 7/1973
(Continued)

OTHER PUBLICATIONS

Dung et al. (Hydroxypropylcellulose polymer molecular weight: Influence of Erodible Modified Release Matrix System, 2011) (Year: 2011).*

(Continued)

*Primary Examiner* — Robert A Wax
*Assistant Examiner* — Melissa S Mercier
(74) *Attorney, Agent, or Firm* — Greenblum & Bernstein, P.L.C.

(57) ABSTRACT

A composite particle comprising from 50 to 80 parts by mass of cellulose, from 10 to 40 parts by mass of an inorganic compound and from 4 to 11 parts by mass of hydroxypropyl cellulose based on 100 parts by mass of a total of contents of the cellulose, the inorganic compound and the hydroxypropyl cellulose.

8 Claims, 1 Drawing Sheet

(51) Int. Cl.
*C08L 1/26* (2006.01)
*A61K 9/20* (2006.01)
*A61K 31/375* (2006.01)
*A23P 10/28* (2016.01)
*A23P 30/10* (2016.01)

(52) U.S. Cl.
CPC .......... *A61K 9/2054* (2013.01); *A61K 9/2095* (2013.01); *A61K 31/375* (2013.01); *A61K 47/38* (2013.01); *C08J 3/12* (2013.01); *C08K 3/00* (2013.01); *C08K 3/22* (2013.01); *C08K 3/34* (2013.01); *C08L 1/02* (2013.01); *C08L 1/26* (2013.01)

(56) References Cited

FOREIGN PATENT DOCUMENTS

| JP | 46-042792 B | | 12/1971 |
|---|---|---|---|
| JP | H08-104650 A | | 4/1996 |
| JP | 2005-232260 A | | 9/2005 |
| JP | 2005232260 A | * | 9/2005 |
| JP | 2009-137892 A | | 6/2009 |
| WO | 2011/065350 A | | 6/2011 |
| WO | 2012/002253 A | | 1/2012 |

OTHER PUBLICATIONS

Supplementary European Search Report issued in corresponding European Application No. 16870506.9 dated Sep. 24, 2018.
International Search Report dated Feb. 14, 2017 for PCT Application No. PCT/JP2016/084657 filed Nov. 22, 2016.
International Preliminary Report on Patentability dated Jun. 5, 2018 for PCT Application No. PCT/JP2016/084657 filed Nov. 22, 2016.
Database entry XP-002784542 providing expert entitled "Hydroxypropyl Cellulose" from Handbook of Pharmaceutical Excipients (Raymond C. Rowe et al, eds. 5th Edition), 2006.

* cited by examiner

COMPOSITE PARTICLES INCLUDING CELLULOSE, INORGANIC COMPOUND, AND HYDROXYPROPYL CELLULOSE

TECHNICAL FIELD

The present invention relates to a composite particle that is excellent in fluidity, that is low in reactivity with an active ingredient, and that can have moldability and fluidity at high levels to thereby allow to be tableted without failure.

The present invention particularly relates to a composite particle suitable for use as an excipient of a molded article.

BACKGROUND ART

Conventionally, a cellulose powder has been widely used as an excipient in preparation of a molded article containing an active ingredient in the fields of pharmaceutical, food and other chemical industries.

A single inorganic compound, however, is restricted in terms of the amount thereof which can be powdered at one time, because of being too large in apparent specific volume. In addition, such an inorganic compound also has the handing problem of being scattered, for example. Therefore, there is studied use of a porous composite particle of cellulose and an inorganic compound, as an excipient.

In a common tablet production method, tableting is made in which a powder is packed in a mortar and subjected to compression molding by a pestle. If a drug is easily attached to the pestle, a phenomenon called "sticking" occurs in which the surface of a molded article is peeled off. While a single inorganic compound is usually used as an excipient, sticking cannot be necessarily prevented by the single inorganic compound. In addition, the single inorganic compound is large in apparent specific volume, and thus is known to have the following problems: easily causes a jet flow during tableting and deteriorates packability in the mortar, resulting in a variation in the weight of a molded article; and a phenomenon called "capping" occurs in which a molded article is partially peeled off.

A cellulose powder, although serving as an excipient high in moldability, is also known to have the following problems: if wetted once, the cellulose powder is deteriorated in moldability and does not exert a function as an excipient; and the cellulose powder is low in liquid retention property as compared with an inorganic compound.

Patent Literature 1 describes a method of providing a composite particle having an apparent specific volume of from 7 to 13 cm$^3$/g, the method including forming and drying a slurry including cellulose and calcium silicate at a specified mass ratio. Patent Literature 1 describes the following: the composite particle is high in liquid retention rate and is high in particle fluidity after liquid retention and thus can be tableted in open feed by a direct tableting method, less causes tableting failure to occur, and is high in moldability.

CITATION LIST

Patent Literature

Patent Literature 1: International Publication No. WO 2012/002253

SUMMARY OF INVENTION

Technical Problem

On the other hand, there has also been recently demanded an excipient low in reactivity with an active ingredient. A conventional excipient has the following problem; if the excipient and an active ingredient high in reactivity therewith are subjected to compression molding, both may be reacted, resulting in a deterioration in whiteness of a molded article to cause the active ingredient to be deactivated and denatured.

In view of the above problems, an object of the present invention is to provide a composite particle having a high moldability, which reduces tableting failure in a direct tableting method, and having a low reactivity with an active ingredient, which is suitable for excipient.

Solution to Problem

The present inventors have made intensive studies in order to solve the above problems, and as a result, have found that a composite particle obtained by composite formation of cellulose, an inorganic compound and hydroxypropyl cellulose is high in particle moldability and fluidity, and, when used as an excipient for a molded article including an active ingredient, is low in reactivity with the active ingredient, thereby leading to completion of the present invention.

That is, the present invention is as described below.

[1]

A composite particle comprising from 50 to 80 parts by mass of cellulose, from 10 to 40 parts by mass of an inorganic compound and from 4 to 11 parts by mass of hydroxypropyl cellulose based on 100 parts by mass of a total of contents of the cellulose, the inorganic compound and the hydroxypropyl cellulose.

[2]

The composite particle according to claim 1, having an apparent specific volume of from 4 to 7 cm$^3$/g.

[3]

The composite particle according to [1] or [2], wherein the inorganic compound is at least one selected from the group consisting of hydrous silicon dioxide, light anhydrous silicic acid, synthetic aluminum silicate, aluminum magnesium hydroxide, magnesium aluminometasilicate, magnesium aluminosilicate, calcium silicate, amorphous silicon oxide hydrate, magnesium silicate and hydrous magnesium silicate.

[4]

The composite particle according to [3], wherein the inorganic compound is calcium silicate.

[5]

The composite particle according to any of [1] to [4], wherein a 2% by mass aqueous solution of the hydroxypropyl cellulose has a viscosity at 20° C. of from 2 to 4000 mPa·s, and the hydroxypropyl cellulose has a molecular weight of from 40000 to 910000.

[6]

The composite particle according to any of [1] to [5], having a weight average particle size of from 20 to 250 μm.

[7]

A molded article comprising the composite particle according to any of [1] to [6], and an active ingredient.

[8]

The molded article according to [7], wherein the active ingredient is an ingredient for a medicine or an ingredient for health food.

Advantageous Effects of Invention

The composite particle of the present invention is small in apparent specific volume, is good in handleability and can allow the weight of a molded article and the content of an active ingredient to be uniform in each molded article, and thus can allow the content of a liquid ingredient in the molded article to be high. Additionally, the present invention can provide a molded article with sufficient hardness, without sticking and capping, and with low friability. Furthermore, the molded article is low in reactivity with an active ingredient.

DESCRIPTION OF EMBODIMENTS

Figure 1:
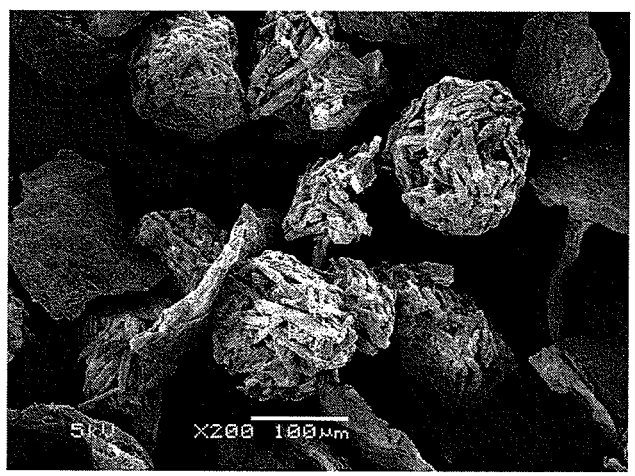
FIG. 1 is a SEM photograph of composite particle A obtained in Example 1.

Hereinafter, an embodiment for carrying out the present invention (hereinafter, also referred to as "the present embodiment".) will be described in detail. Herein, the present invention is not intended to be limited to the following present embodiment, and can also be variously modified and carried out within the gist thereof.

A composite particle of the present embodiment contains cellulose, an inorganic compound and hydroxypropyl cellulose.

In the present embodiment, the cellulose means polysaccharide where glucose units are linked by β-1,4-glucoside bond, and is a compound represented by $(C_6H_{10}O_5)_n$. In the present embodiment, the cellulose may be a fibrous substance including a natural polymer obtained from a natural source, or may be synthesized cellulose or regenerated cellulose.

In the present embodiment, the cellulose preferably has a cellulose I type crystal structure.

In the composite particle of the present embodiment, the cellulose is preferably contained in the form of a particle, and, in particular, preferably has an average width of from 2 to 30 μm and an average thickness of from 0.5 to 5 μm. When the average width and the average thickness of such a cellulose particle fall within the above ranges, the cellulose particle can be formed, together with an inorganic compound and hydroxypropyl cellulose, into a composite, thereby allowing a pore to be sufficiently developed in the composite particle. Further preferably, the cellulose particle has an average width of from 2 to 25 μm and an average thickness of from 1 to 5 μm.

In the present embodiment, the cellulose may also be crystalline cellulose. Herein, the crystalline cellulose means a white crystalline powder, and is formed by partially depolymerizing α-cellulose obtained as a pulp from a fibrous plant, with a mineral acid or the like, and purifying the resultant. The crystalline cellulose is available at any of various grades, and crystalline cellulose having a polymerization degree of from 100 to 450 is preferable in the present embodiment. Examples of a commercially available product which can be used include "Ceolus" PH Grade, KG Grade and UF Grade (all produced by Asahi Kasei Chemicals Corporation), and most preferable is KG Grade.

The average volume particle size of the cellulose particle is preferably from 10 to 100 μm, preferably from 10 to 50 μm, further preferably from 10 to 40 μm.

The average polymerization degree of the cellulose is preferably from 10 to 450, further preferably from 150 to 450.

In the present embodiment, the composite particle contains an inorganic compound.

The inorganic compound is preferably insoluble in water and preferably has an apparent specific volume of from 10 to 50 $cm^3/g$. Specific examples include hydrous silicon dioxide, light anhydrous silicic acid, synthetic aluminum silicate, aluminum magnesium hydroxide, magnesium aluminometasilicate, magnesium aluminosilicate, calcium silicate, amorphous silicon oxide hydrate, magnesium silicate and hydrous magnesium silicate.

The inorganic compound preferably has a particle shape, and the average volume particle size thereof is preferably from 10 to 50 μm from the viewpoint that the concentration of a dispersion liquid of the cellulose and the inorganic compound can be increased.

The inorganic compound is particularly preferably calcium silicate. Calcium silicate is preferably configured from CaO, $SiO_2$ and $H_2O$, and, in particular, preferably represented by chemical formula: $2CaO.3SiO_2.mSiO_2.nH_2O$ (1<m<2, 2<n<3). Examples of a commercially available product include Florite R (trade name) (produced by Tomita Pharmaceutical Co., Ltd.), Florite RE (trade name) (including 50% or more of $CaO_2$ and 22% or more of CaO, sold by Tomita Pharmaceutical Co., Ltd.), and CALCIUM CILICATE (trade name) (produced by Priti Industries).

In general, calcium silicate is a white powder and is insoluble in water. Calcium silicate is a substance having a high liquid absorption ability and being good in moldability. The average volume particle size is from 10 to 40 further preferably from 20 to 30 μm.

The composite particle of the present embodiment includes hydroxypropyl cellulose.

The hydroxypropyl cellulose has an ability as a binder, and is thus considered to contribute to maintaining of a composite form of the cellulose and the inorganic compound, to thereby allow a granulated form to be set. However, the mechanism where the effect due to inclusion of the hydroxypropyl cellulose is exerted is not limited to the above.

The hydroxypropyl cellulose is preferably one having high bindability, and examples of such hydroxypropyl cellulose include Klucel™ (trade name) produced by Ashland Inc., and Celny (trade name) produced by Nippon Soda Co., Ltd.

In the present embodiment, the hydroxypropyl cellulose is preferably soluble in water. Furthermore, when the hydroxypropyl cellulose is formed into a 2% by mass aqueous solution, the aqueous solution preferably has a viscosity at 20° C. of from 2 to 4000 mPa·s, and the hydroxypropyl cellulose preferably has a molecular weight of from 40000 to 910000 (GPC method).

More preferably, the 2% by mass aqueous solution of the hydroxypropyl cellulose has a viscosity at 20° C. of from 6 to 10 mPa·s, and the hydroxypropyl cellulose has a molecular weight of from 110000 to 610000 (GPC method).

It is considered that as the apparent specific volume and the specific surface area of the inorganic compound are larger, the composite particle of the present embodiment can exhibit more excellent effect of preventing sticking in producing a molded article when it is used as an excipient, and light anhydrous silicic acid has larger apparent specific volume and specific surface area than calcium silicate. It, however, has been revealed from studies about the inorganic compound to be used together with the cellulose and the hydroxypropyl cellulose in the present embodiment that the most excellent effect of preventing sticking is exerted in the case of use of calcium silicate.

Furthermore, the present inventors have found that an excipient formed from a composite particle obtained by forming an inorganic compound and hydroxypropyl cellulose together with cellulose into a composite and setting the apparent specific volume to be as small as possible can provide a molded article having a sufficient hardness, causing neither sticking nor capping, having a low friability, and having reduced reactivity with an active ingredient.

In the present embodiment, the contents of the cellulose, the inorganic compound and the hydroxypropyl cellulose included in the composite particle are from 50 to 80 parts by mass, from 10 to 40 parts by mass and from 4 to 11 parts by mass, respectively, based on 100 parts by mass of the total thereof.

Preferably, the contents of the cellulose, the inorganic compound and the hydroxypropyl cellulose are from 60 to 70 parts by mass, from 10 to 40 parts by mass and from 5 to 10 parts by mass, respectively. Further preferably, the contents of the cellulose, the inorganic compound and the hydroxypropyl cellulose are from 60 to 65 parts by mass, from 25 to 35 parts by mass and from 5 to 10 parts by mass, respectively.

If the content of the hydroxypropyl cellulose in the composite particle is less than 4 parts by mass, sticking occurs in a molded article obtained by using such a composite particle as an excipient. In addition, if no hydroxypropyl cellulose is added to the composite particle, it is considered that the disintegration time of a molded article obtained by using such a composite particle as an excipient is longer about 4 times than that of a molded article including the hydroxypropyl cellulose, thereby resulting in an increase in reactivity with an active ingredient.

In the present embodiment, the composite particle refers to a particle including the cellulose, the inorganic compound and the hydroxypropyl cellulose therein, and is preferably formed as one aggregate (namely, composite particle) where a plurality of particles of each of the cellulose, the inorganic compound and the hydroxypropyl cellulose are aggregated to form a particle larger than each of the particles.

Figure 2:
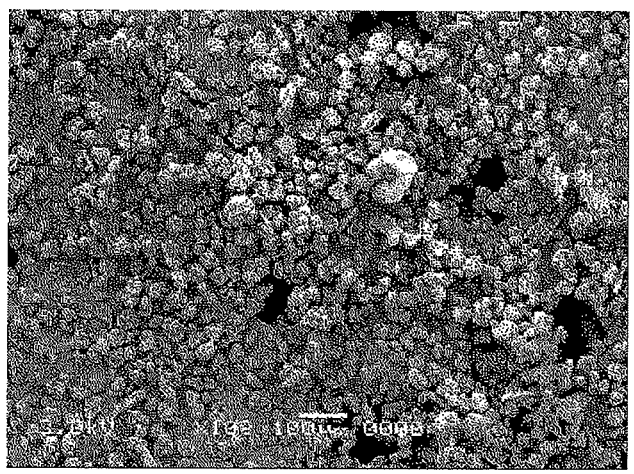
FIG. 2 is a SEM photograph of a mixture of primary particles of cellulose, an inorganic compound and hydroxypropyl cellulose.

FIG. 1 illustrates a SEM photograph of one example of such an aggregate (composite particle). FIG. 1 is obtained by observation of a composite particle of Examples by use of SEM (at a magnification of from 200 to 500 times). In FIG. 1, a plurality of particles of each of the cellulose, the inorganic compound and the hydroxypropyl cellulose are observed, and they are aggregated to form one aggregate (composite particle). FIG. 2, in which respective particles of the cellulose, the inorganic compound and the hydroxypropyl cellulose are simply mixed, is shown for comparison.

The aggregate is larger than respective particles of the cellulose, the inorganic compound and the hydroxypropyl cellulose. On the other hand, in a simple mixture of respective powders of the cellulose, the inorganic compound and the hydroxypropyl cellulose, respective primary particles separately present and does not form any aggregate (composite particle). Therefore, even if such primary particles are simply mixed, an excipient having excellent moldability and fluidity like the composite particle of the present embodiment cannot be obtained.

In the present embodiment, the apparent specific volume of the composite particle is preferably from 4 to 7 $cm^3/g$. When the apparent specific volume is 4 $cm^3/g$ or more and 7 $cm^3/g$ or less, an increase in jet properties is suppressed, and thus, in producing a molded article by mixing with an active ingredient, a variation in the content of the active ingredient and a deterioration in moldability are suppressed.

The composite particle of the present embodiment is large in apparent specific volume, high in liquid retention rate and excellent in fluidity. Furthermore, the composite particle can be suitably used in a direct tableting method and a wet tableting method, does not easily scatter and excellent in operationability, and thus can prevent tableting failures such as sticking and capping.

The composite particle of the present embodiment is particularly suitable for use as an excipient in formation of a molded article such as a tablet, including an active ingredient with low fluidity, which is hard to achieve high tablet hardness, and specific examples of such an active ingredient include a self-medication product such as a cold medicine, an extract powder for Chinese medicines, and a drug of enzyme/protein, which is easily deactivated by tableting pressure/friction against an excipient.

The composite particle is also suitable as an excipient in production of a tablet easily causing tableting failures such as breaking, chipping, internal peeling and cracking of the tablet surface. Specific examples of such a tablet include a small tablet, a non-circular deformed tablet having a portion where the compression pressure is hardly applied in a uniform manner, such as a constriction at the edge, a tablet including various drugs in large amounts, and a coating granule-containing tablet.

Hereinafter, one example of the method of producing the composite particle of the present embodiment will be described.

The composite particle of the present embodiment can be obtained by preparing a dispersion liquid including the cellulose, the inorganic compound and the hydroxypropyl cellulose (dispersing the cellulose, the inorganic compound and the hydroxypropyl cellulose in a medium), and drying the dispersion liquid. The composite particle can also be obtained by another method including strongly stirring the cellulose, the inorganic compound and the hydroxypropyl cellulose in a wet manner (so-called composite formation or Coprocessing).

First, the method of preparing the cellulose is described.

A raw material of the cellulose is generally a cellulose-containing natural product, and examples thereof include wood, bamboo, straw, rice straw, cotton, ramie, bagasse, kenaf, beet, sea squirt and bacteria cellulose. Such raw materials may be of plant or animal origin, and may be used as a mixture of two or more thereof. Such raw materials may also be hydrolyzed. In particular, examples of such hydrolysis include acid hydrolysis, alkali oxidative degradation, hydrothermal degradation and steam explosion, and two or more thereof may be used in combination.

A medium for dispersing a solid including the cellulose in hydrolysis is not particularly limited, and any medium industrially used can be used, and water or an organic solvent can be used. Examples of the organic solvent include alcohols such as methanol, ethanol, isopropyl alcohol, butyl alcohol, 2-methylbutyl alcohol and benzyl alcohol, hydrocarbons such as pentane, hexane, heptane and cyclohexane, and ketones such as acetone and ethyl methyl ketone. In particular, the organic solvent is preferably one for use in pharmaceutical products, and examples include those classified as solvents in "Iyakuhin Tenkazai Jiten (Pharmaceutical Additive Dictionary)" (published by Yakuji Nippo Limited). The medium is preferably water. Water and such organic solvents may be used in combinations of two or more thereof. The solid may be dispersed in one medium once, and thereafter the medium may be removed and the solid may be dispersed in a different medium.

In the present embodiment, the cellulose preferably has a particle shape having an average width of from 2 to 30 μm and an average thickness of from 0.5 to 5 μm.

A cellulose particle having such a shape can be obtained by, for example, tearing a raw material cellulose mainly in the longitudinal direction, and, more specifically, a cellulose particle whose average width and average thickness are controlled in specified ranges can be obtained by, for example, a method including treating a wood pulp by a high-pressure homogenizer, and, if necessary, subjecting the resultant to a mechanical treatment such as grinding or a classification treatment, or an appropriate combination of both the treatments. Alternatively, for example, a pulp where the average width and the average thickness of the cellulose particle are from 2 to 30 μm and from 0.5 to 5 μm, respectively, may be sorted out and used.

In the present embodiment, the cellulose particle being dispersed in water preferably has an average volume particle size of from 10 to 100 μm, preferably from 10 to 50 μm, further preferably from 10 to 40 μm.

Examples of the method of providing the cellulose particle being dispersed in water, having an average volume particle size of from 10 to 100 μm, include the following.

i) A method including subjecting the cellulose to shearing, grinding, crushing and pulverizing to adjust the particle size.
ii) A method including subjecting the cellulose to a high-pressure treatment such as a blasting treatment, dividing the cellulose particle in a long axis direction, and, if necessary, applying a shear force thereto, to adjust the particle size.
iii) A method including subjecting the cellulose to a chemical treatment, to adjust the particle size.

Any one of the above methods may be adopted, or two or more of the above methods may be used in combination. Methods i) and ii) above may be performed in a wet manner or a dry manner, or in a combination manner.

Examples of the shearing method in methods i) and ii) above include a shearing method using a portable mixer, a three-dimensional mixer, a side-wall mixer or the like of a one-direction rotation type, multi-axis rotation type, reciprocal inversion type, vertical movement type, rotation+ vertical movement type or piping type stirring blade, a jet type stirring shearing method using a line mixer or the like, a treatment method using a high-shear homogenizer, a high-pressure homogenizer, an ultrasonic homogenizer or the like, and an axial rotation extrusion type shearing method using a kneader or the like.

Examples of the pulverizing method in method i) above include a screen type pulverizing method using a screen mill, a hammer mill or the like, a blade rotation shearing screen type pulverizing method using a flush mill or the like, an air stream type pulverizing method using a jet mill or the like, a ball type pulverizing method using a ball mill, a vibratory ball mill or the like, and a blade stirring type pulverizing method. The above methods may be used in combinations of two or more thereof.

Furthermore, the average volume particle size of the cellulose particle can also be controlled within a desired range by adjusting the condition of a step of hydrolyzing or dispersing the cellulose, in particular, a stirring force of a solution including the cellulose.

In general, if the acid and alkali concentrations and the reaction temperature of a hydrolysis solution are increased, the polymerization degree of cellulose tends to be decreased and the average volume particle size of cellulose in a dispersion liquid tends to be decreased. In addition, if the stirring force of a solution is stronger, the average volume particle size of a cellulose particle tends to be smaller.

Next, the step of preparing the dispersion liquid including the cellulose, the inorganic compound and the hydroxypropyl cellulose will be described.

The dispersion liquid can be prepared by dispersing the cellulose, the inorganic compound and the hydroxypropyl cellulose in a medium.

Specifically, examples include the following methods.
i) A method including mixing the cellulose, the inorganic compound and the hydroxypropyl cellulose in advance, and adding the mixture to a medium, to provide the dispersion liquid.
ii) A method including adding the inorganic compound and the hydroxypropyl cellulose to a cellulose dispersion liquid, to provide the dispersion liquid.
iii) A method including adding the hydroxypropyl cellulose and the cellulose to a dispersion medium to form a dispersion liquid, and adding the inorganic compound thereto, to provide the dispersion liquid.
iv) A method including adding and mixing the hydroxypropyl cellulose to and with a cellulose dispersion liquid, and adding the inorganic compound to the mixture, to provide the dispersion liquid.
v) A method including adding the cellulose and the hydroxypropyl cellulose to an inorganic compound dispersion liquid, to provide the dispersion liquid.

The medium (dispersion medium) of the dispersion liquid is not limited, any of various organic solvents can be used, and examples include ethanol and isopropyl alcohol.

The method of adding respective ingredients is not particularly limited, and any method commonly performed can be used. Specifically, examples include an adding method using a small size suction transport apparatus, an air transport apparatus, a bucket conveyor, a pneumatic transport apparatus, a vacuum conveyer, a vibration type quantitative metering feeder, a spray, a funnel, or the like. Such ingredients may be continuously added or collectively loaded.

The mixing method is not particularly limited, and any method commonly performed can be used. Specifically, a vessel rotation type mixer such as a V-type, W-type, double cone type or container tack type mixer, a stirring type mixer such as a high speed stirring type, universal stirring type, ribbon type, pug type or Nauta-type mixer, a high speed fluid type mixer, a drum type mixer, or a fluidized bed type mixer may be used. Alternatively, a dispersing method using a vessel shaking type mixer such as a shaker, or a portable mixer, a three-dimensional mixer, a side-wall mixer or the like of a one-direction rotation type, multi-axis rotation type, reciprocal inversion type, vertical movement type, rotation+ vertical movement type or piping type stirring blade, a jet type stirring/dispersing method using a line mixer or the like, a treatment method using a high-shear homogenizer, a high-pressure homogenizer, an ultrasonic homogenizer or the like, or an axial rotation extrusion type shearing method using a kneader or the like may be used, and two or more thereof may be used in combination.

The total concentration of the cellulose, the inorganic compound and the hydroxypropyl cellulose in the dispersion liquid obtained by the above operation is preferably from 5 to 40% by mass. The total concentration is preferably 5% by mass or more in terms of fluidity of the composite particle obtained by drying of the dispersion liquid, and is preferably 40% by mass or less in terms of compression moldability. The total concentration is more preferably from 5 to 30% by mass, further preferably from 5 to 20% by mass.

Next, the step of drying the dispersion liquid including the cellulose, the inorganic compound and the hydroxypropyl cellulose will be described.

The dispersion liquid obtained by the above operation is dried to thereby provide the composite particle of the present embodiment. The drying method is not particularly limited, and examples thereof include lyophilization, spray drying, drum drying, shelf drying, air stream drying and vacuum drying. These may be used in combinations of two or more. The spray method in spray drying may be any spray method such as disc type, pressure nozzle, pressurized two-fluid nozzle and pressurized four-fluid nozzle spray methods, and these may be used in combinations of two or more.

Herein, when the above spray drying is adopted, traces of a water-soluble polymer and a surfactant may be added to the dispersion liquid for the purpose of a decrease in surface tension of the dispersion liquid, or a foaming agent, a gas generating substance, or gas may be added to the dispersion liquid for the purpose of an increase in vaporization rate of the medium. Specific examples of the water-soluble polymer, the surfactant, the foaming agent, the gas generating substance and the gas are shown below. Herein, the water-soluble polymer, the surfactant and the gas generating substance may be added before drying, and the order of addition thereof is not particularly limited. Such respective substances may be used in combinations of two or more thereof.

Examples of the water-soluble polymer include water-soluble polymers described in "Iyakuhin Tenkazai Jiten (Pharmaceutical Additive Dictionary)" (published by Yakuji Nippo Limited), such as hydroxypropyl cellulose, hydroxypropyl methylcellulose, polyacrylic acid, a carboxy vinyl polymer, polyethylene glycol, polyvinyl alcohol, polyvinylpyrrolidone, methylcellulose, gum arabic and starch paste.

Examples of the surfactant include those classified as surfactants in "Iyakuhin Tenkazai Jiten (Pharmaceutical Additive Dictionary)" (published by Yakuji Nippo Limited), such as phospholipid, glycerin fatty acid ester, polyethylene glycol fatty acid ester, sorbitan fatty acid ester, polyoxyethylene hardened castor oil, polyoxyethylene cetyl ether, polyoxyethylene stearyl ether, polyoxyethylene nonyl phenyl ether, polyoxyethylene polyoxypropylene glycol, polyoxyethylene sorbitan monolaurate, polysorbate, sorbitan monooleate, glyceride monostearate, monooxyethylene sorbitan monopalmitate, monooxyethylene sorbitan monostearate, polyoxyethylene sorbitan monooleate, sorbitan monopalmitate and sodium lauryl sulfate.

Examples of the foaming agent include foaming agents described in "Iyakuhin Tenkazai Jiten (Pharmaceutical Additive Dictionary)" (published by Yakuji Nippo Limited), such as tartaric acid, sodium hydrogen carbonate, potato starch, anhydrous citric acid, medical soap, sodium lauryl sulfate, lauric acid diethanolamide and Lauromacrogol.

Examples of the gas generating substance include bicarbonates that generate gas by pyrolysis, such as sodium hydrogen carbonate and ammonium hydrogen carbonate, and carbonates that generate gas by a reaction with an acid, such as sodium carbonate and ammonium carbonate. Herein, when such carbonates are used, these are preferably used with an acid. Examples of the acid include organic acids such as citric acid, acetic acid, ascorbic acid and adipic acid, protonic acid such as hydrochloric acid, sulfuric acid, phosphoric acid and nitric acid, and Lewis acids such as boron fluoride. In particular, an acid for use in pharmaceutical products and/or foods is preferable.

With respect to the gas, the dispersion liquid may be impregnated with gas such as nitrogen, carbon dioxide, liquefied petroleum gas or dimethyl ether.

The composite particle of the present embodiment is formed by simultaneously drying the cellulose, the inorganic compound and the hydroxypropyl cellulose being present in a dispersion liquid. It is considered that, when the medium is evaporated with the cellulose, the inorganic compound and the hydroxypropyl cellulose being uniformly associated, the capillary condensation action occurs to densely aggregate the cellulose, the inorganic compound and the hydroxypropyl cellulose. Such an aggregate structure cannot be obtained by separately drying each of the cellulose, the inorganic compound or the hydroxypropyl cellulose and mixing each other since compounding thereof does not occur.

Herein, when the cellulose particle in the dispersion liquid has any average width and any average thickness falling within the previously specified ranges, in particular, the effect of suppressing excessive particle aggregation due to capillary condensation during drying is highly exerted, thereby enabling a pore having a large volume to be formed in the composite particle.

Herein, when the composite particle is produced by the above method, a single cellulose particle, a single inorganic compound particle or a single hydroxypropyl cellulose particle may also remain in the obtained powder of the composite particle, but the powder may be used as it is without any separation of such particles.

A molded article of the present embodiment includes the composite particle of the present embodiment, and an active ingredient, and can be produced by, for example, molding a mixture of the composite particle of the present embodiment and an active ingredient. Hereinafter, the molded article of the present embodiment will be described.

The contents of the active ingredient and the composite particle in the molded article of the present embodiment are not particularly limited, and for example, the active ingredient can be used in the range from 0.001 to 99% by mass, and the composite particle can be used in the range from 1 to 99.999% by mass. The content of the active ingredient is preferably 0.001% by mass or more from the viewpoint that the effect of the active ingredient is ensured, and the content is preferably 99% by mass or less in terms of practical hardness, friability and disintegration property. More preferably, the molded article includes from 1 to 90% by mass of the composite particle.

When the active ingredient is in the form of a liquid (for example, in the form of a liquid at 25° C.), tableting failures such as sticking and capping occur, and therefore the content of the active ingredient in the molded article is limited. The composite particle of the present embodiment, however, simultaneously has high liquid retention property and high moldability, and therefore, when the composite particle of the present embodiment is used as an excipient, more than 20% by mass of the liquid ingredient can be compounded into the molded article. The content of the liquid active ingredient is preferably from 21 to 50% by mass, particularly preferably from 21 to 30% by mass.

The content of tocopherol acetate in a currently commercially available molded article is at most 100 mg/500 mg of the total amount of the tablet, and there is not found any one to which more than 20% by mass of tocopherol acetate is compounded. The composite particle of the present embodiment can be used to allow the content of the liquid active ingredient to be more than 20% by mass. For example, when the liquid active ingredient is compounded, in an amount of from 21 to 50% by mass, to the commercially available tocopherol acetate tablet, the active ingredient can be in a certain amount (100 mg) to thereby provide a small size molded article whose amount falls within the range from 250 to 480 mg, and on the contrary, the tablet can be in a certain weight (500 mg) to thereby allow the amount of the liquid active ingredient to be increased within the range from 105 to 250 mmg.

The content of tocopherol acetate per tablet is preferably 120 to 200 mg, further preferably from 120 to 150 mg.

The molded article of the present embodiment can be processed by a known method such as granulation, sizing or tableting. In particular, the composite particle of the present embodiment is suitable for molding by tableting. When the composite particle of the present embodiment and the active ingredient are included within the above ranges, a molded article having sufficient hardness can be produced by a direct tableting method. The composite particle of the present embodiment is also suitable for, in addition to a direct tableting method, a dry granule compression method, a wet granule compression method, a post-formation method of a powder, a method of producing a multicore tablet using a tablet prepared by compression molding in advance as an inner core, a method including stacking a plurality of molded articles compressed in advance and compressing them again to produce a multilayer tablet, and the like.

In the present embodiment, the active ingredient refers to a substance exhibiting physiological activity, and examples thereof include an ingredient for a pharmaceutical product, an ingredient for health food, a pesticide ingredient, a fertilizer ingredient, a livestock food ingredient, a food ingredient, a cosmetic ingredient, a dye, a flavoring agent, a metal, ceramics, a catalyst and a surfactant. A suitable active ingredient is an ingredient for a pharmaceutical product or an ingredient for health food.

Examples of the ingredient for a pharmaceutical product include an antipyretic, analgesic and anti-inflammatory agent, a sedative-hypnotic agent, a drowsiness preventing agent, a dizziness suppressing agent, a children's analgesic agent, a stomachic, an antacid, a digestant, a cardiotonic drug, an anti-arrhythmic drug, an antihypertensive drug, a vasodilator, a diuretic drug, an anti-ulcerative drug, an intestinal drug, an osteoporosis therapeutic drug, an antitussive drug, an antiasthmatic drug, an antimicrobial agent, a pollakiuria ameliorating agent, a revitalizer and a vitamin supplement, and one orally administered is preferable.

The ingredient for a pharmaceutical product may be used singly or in combinations of two or more thereof. Specific examples can include ingredients for pharmaceutical products, described in "Japanese Pharmacopeia", "Japanese Pharmaceutical Codex", "USP", "NF" and "EP", such as aspirin, aspirin aluminum, acetaminophen, ethenzamide, sasapyrine, salicylamide, lactylphenetidin, isotibenzyl hydrochloride, diphenylpyraline hydrochloride, diphenhydramine hydrochloride, difeterol hydrochloride, triprolidine hydrochloride, tripelenamine hydrochloride, thonzylamine hydrochloride, fenethazine hydrochloride, methdilazine hydrochloride, diphenhydramine salicylate, carbinoxamine diphenyldisulfonate, alimemazine tartrate, diphenhydramine tannate, diphenylpyraline teoclate, mebhydrolin napadisylate, promethazine methylenedisalicylate, carbinoxamine maleate, chlorpheniramine dl-maleate, chlorpheniramine d-maleate, difeterol phosphate, alloclamide hydrochloride, cloperastine hydrochloride, pentoxyverine citrate (carbetapentane citrate), tipepidine citrate, dibunate sodium, dextromethorphan hydrobromide, dextromethorphan-phenolphthalic acid, tipepidine hibenzate, chloperastine fendizoate, codeine phosphate, dihydrocodeine phosphate, noscapine hydrochloride, noscapine, dl-methylephedrine hydrochloride, a dl-methylephedrine saccharin salt, potassium guaiacolsulfonate, guaifenesin, caffeine sodium benzoate, caffeine, anhydrous caffeine, vitamin B1 and its derivatives and their salts, vitamin B2 and its derivatives and their salts, vitamin C and its derivatives and their salts, hesperidin and its derivatives and their salts, vitamin B6 and its derivatives and their salts, nicotinic acid amide, calcium pantothenate, aminoacetic acid, magnesium silicate, synthetic aluminum silicate, synthetic hydrotalcite, magnesium oxide, dihydroxyaluminum-aminoacetate (aluminum glycinate), aluminium hydroxide gel (as dried aluminium hydroxide gel), dried aluminium hydroxide gel, aluminium hydroxide-magnesium carbonate mixed dried gel, an aluminum hydroxide-sodium hydrogen carbonate coprecipitation product, an aluminum hydroxide-calcium carbonate-magnesium carbonate coprecipitation product, a magnesium hydroxide-potassium aluminum sulfate coprecipitation product, magnesium carbonate, magnesium aluminometasilicate, ranitidine hydrochloride, cimetidine, famotidine, naproxen, diclofenac sodium, piroxicam, azulene, indometacin, ketoprofen, ibuprofen, difenidol hydrochloride, diphenylpyraline hydrochloride, diphenhydramine hydrochloride, promethazine hydrochloride, meclizine hydrochloride, dimenhydrinate, diphenhydramine tannate, fenethazine tannate, diphenylpyraline teoclate, diphenhydramine fumarate, promethazine methylenedisalicylate, scopolamine hydrobromide, oxyphencyclimine hydrochloride, dicyclomine hydrochloride, methixene hydrochloride, atropine methylbromide, anisotropine methylbromide, spocolamine methylbromide, methyl-1-hyoscyamine bromide, methylbenactyzium bromide, belladonna extract, isopropamide iodide, diphenylpiperidinomethyldioxolan iodide, papaverine hydrochloride, aminobenzoic acid, cesium oxalate, ethyl piperidinoacetylaminobenzoate, aminophyllin, diprophylline, theophylline, sodium hydrogen carbonate, fursultiamine, isosorbide nitrate, ephedrine, cefalexin, ampicillin, sulfixazole, sucralfate, allyl isopropylacetyl urea, bromovalerylurea and the like, ephedra herb, nandina fruit, yellow bark, polygala root, licorice, platycodon root, plantago seed, plantago herb, senega root, fritillaria, fennel, phellodendron bark, coptis rhizome, zedoary, matricaria, cinnamon bark, gentian, oriental bezoar, beast gall (including bear bile), adenophrae radix, ginger, atractylodes lancea rhizome, clove, citrus unshiu peel, atractylodes rhizome, earthworm, panax rhizome, ginseng, japanese valerian, moutan bark, zanthoxylum fruit and extracts thereof, insulin, vasopressin, interferon, urokinase, serratio peptidase, and somatostatin, and the above may be used singly or in combinations of two or more thereof.

The ingredient for health food is not limited, and any ingredient to be compounded for the purpose of health promotion can be used. Examples thereof include green juice powder, aglycone, agaricus, ashwagandha, astaxanthin, acerola, aminoacids (valine, leucine, isoleucine, lysine, methionine, phenylalanine, threonine, tryptophan, histidine, cystine, tyrosine, arginine, alanine, aspartic acid, seaweed powder, glutamine, glutamic acid, glycin, proline, serine and the like), alginic acid, *Ginkgo biloba* extract, sardine peptide, turmeric, uronic acid, echinacea, siberian ginseng, oligosaccharide, oleic acid, nucleoprotein, dried bonito peptide, catechin, potassium, calcium, carotenoid, *Garcinia cambogia*, L-carnitine, chitosan, conjugated linoleic acid, *Aloe arborescens, Gymnema sylvestre* extract, citric acid, *Orthosiphon stamineus*, glyceride, glycenol, glucagon, curcumin, glucosamine, L-glutamine, chlorella, cranberry extract, *Uncaria tomentosa*, germanium, enzyme, Korean ginseng extract, coenzyme Q10, collagen, collagen peptide, *Coleus blumei*, chondroitin, psyllium husk powder, *Crataegi* fructus extract, saponin, lipid, L-cystine, Japanese basil extract, citrimax, fatty acid, phytosterol, seed extract, spirulina, squalene, *Salix alba*, ceramide, selenium, St. John's wort extract, soybean isoflavone, soybean saponin, soybean peptide, soybean lecithin, monosaccharide, protein, chaste tree extract, iron, copper, docosahexaenoic acid, tocotrienol, nattokinase, *Bacillus natto* culture extract, sodium niacin, nicotine acid, disaccharide, lactic acid bacterium, garlic, saw palmetto, sprouted rice, pearl barley extract, herb extract, valerian extract, pantothenic acid, hyaluronic acid, biotin, chromium picolinate, vitamins A and A2, vitamins B1, B2 and B6, vitamin B12, vitamin C, vitamin D, vitamin E, vitamin K, hydroxytyrosol, *Bifidobacterium*, beer yeast, fructo oligosaccharide, flavonoid, Butcher's broom extract, black cohosh, blueberry, prune extract, proanthocyanidin, protein, propolis, bromelain, probiotics, phosphatidylcholine, phosphatidylserine, β-carotene, peptide, safflower extract, *Grifola frondosa* extract, maca extract, magnesium, milk thistle, manganese, mitochondria, mineral, mucopolysaccharide, melatonin, *Fomes yucatensis*, melilot extract powder, molybdenum, vegetable powder, folic acid, lactose, lycopene, linolic acid, lipoic acid, phosphorus, lutein, lecithin, rosmarinic acid, royal jelly, DHA and EPA.

The active ingredient may be any form such as a powder form, a crystal form, a liquid form or a semi-solid form, and a liquid active ingredient is suitable. An active ingredient subjected to coating or capsulation for the purposes of elution control, a reduction in bitterness, and the like may also be adopted. An active ingredient dissolved, suspended or emulsified in a medium may also be used. The active ingredients may be used in combination of a plurality thereof.

Examples of the liquid active ingredient include ingredients for pharmaceutical products, described in "Japanese Pharmacopeia", "Japanese Pharmaceutical Codex", "USP", "NF" and "EP", such as teprenone, indomethacin-farnesyl, menatetrenone, phytonadione, vitamin A oil, fenipentol, vitamins such as vitamin D and vitamin E, higher unsaturated fatty acids such as DHA (docosahexaenoic acid), EPA (eicosapentaenoic acid) and liver oil, coenzyme Q, and oil-soluble flavors such as orange oil, lemon oil and peppermint oil. In addition, vitamin E has various homologues and derivatives, examples can include dl-α-tocopherol, dl-α-tocopherol acetate, tocopherol acetate and d-α-tocopherol acetate, and vitamin E is not particularly limited as long as it is in the form of a liquid at 25° C., preferably having a viscosity ranging from 3 to 10000 mPa·s. Vitamin E having a proper viscosity is preferable because moldability and fluidity of the composite particle after the liquid ingredient is supported on the composite are well-balanced. Particularly preferable is tocopherol acetate.

Examples of the semi-solid active ingredient can include Chinese medicines or crude drug extracts such as earthworm, licorice, cinnamon bark, peony root, moutan bark, japanese valerian, zanthoxylum fruit, ginger, citrus unshiu peel, ephedra herb, nandina fruit, yellow bark, polygala root, platycodon root, plantago seed, plantago herb, shorttube lycoris, senega, fritillaria, fennel, phellodendron bark, coptis rhizome, zedoary, matricaria, gentian, oriental bezoar, beast gall, adenophrae radix, ginger, atractylodes lancea rhizome, clove, citrus unshiu peel, atractylodes rhizome, panax rhizome, ginseng, kakkonto, keishito, kousosan, saiko-keishito, shosaikoto, shoseiryuto, bakumondoto, hangekobokuto and maoto, an oyster meat essence, propolis and propolis extract, and coenzyme Q.

The crystal forms of the active ingredient before and after molding may be same or different from each other, and both the crystal forms are preferably the same in terms of stability.

The molded article of the present embodiment freely includes, in addition to the active ingredient and the composite particle, if necessary, additive(s) such as other excipient, a disintegrant, a binder, a fluidizing agent, a lubricant, a corrigent, a flavoring agent, a colorant and a sweetener. Such additives may be used in combinations of two or more thereof.

Examples of such other excipient include those classified as excipients in "Iyakuhin Tenkazai Jiten (Pharmaceutical Additive Dictionary)" (published by Yakuji Nippo Limited), such as starch acrylate, L-aspartic acid, aminoethylsulfonic acid, aminoacetic acid, candy (powder), gum arabic, gum arabic powder, alginic acid, sodium alginate, pregelatinized starch, inositol, ethyl cellulose, an ethylene-vinyl acetate copolymer, sodium chloride, olive oil, kaolin, cacao butter, casein, fructose, a pumice stone granule, carmellose, carmellose sodium, hydrous silicon dioxide, dry yeast, dried aluminium hydroxide gel, dried sodium sulfate, dried magnesium sulfate, agar, agar powder, xylitol, citric acid, sodium citrate, disodium citrate, glycerin, calcium glycerophosphate, sodium gluconate, L-glutamine, clay, a clay grain, croscarmellose sodium, crospovidone, magnesium aluminosilicate, calcium silicate, magnesium silicate, light anhydrous silicic acid, light liquid paraffin, powdered cinnamon bark, crystalline cellulose, crystalline cellulose-carmellose sodium, crystalline cellulose (grain), brown rice malt, synthetic aluminum silicate, synthetic hydrotalcite, sesame oil, wheat flour, wheat starch, wheat germ powder, rice powder, rice starch, potassium acetate, calcium acetate, cellulose acetate phthalate, safflower oil, white beeswax, zinc oxide, titanium oxide, magnesium oxide, β-cyclodextrin, dihydroxyaluminum aminoacetate, 2,6-di-butyl-4-methylphenol, dimethylpolysiloxane, tartaric acid, potassium hydrogen tartrate, plaster, sucrose fatty acid ester, aluminum magnesium hydroxide, aluminium hydroxide-gel, an aluminium hydroxide-sodium hydrogen carbonate co-precipitate, magnesium hydroxide, squalane, stearyl alcohol, stearic acid, calcium stearate, polyoxyl stearate, magnesium stearate, purified gelatine, purified shellac, purified saccharose, purified white soft sugar spherical granule, cetostearyl alcohol, polyethylene glycol 1000 monocetyl ether, gelatine, sorbitan fatty acid ester, D-sorbitol, tricalcium phosphate, soybean oil, unsaponified soybean, soybean lecithin, powdered skim milk, talc, ammonium carbonate, calcium carbonate, magnesium carbonate, neutral anhydrous sodium sulfate, low substitution degree hydroxypropyl cellulose, dextran, dextrin, natural aluminum silicate, corn starch, powdered tragacanth, silicon dioxide, Newkalgen 204, calcium lactate, lactose, Perfiller 101, white shellac, white vaseline, white clay, white soft sugar, a white soft sugar-starch spherical granule, a naked barley green leaf extract powder, dried powder of bud and leaf juice of naked barley, honey, paraffin, potato starch, semi-digested starch, human serum albumin, hydroxypropyl starch, hydroxypropyl cellulose, hydroxypropyl cellulose, hydroxypropyl methylcellulose phthalate, phytic acid, glucose, glucose hydrate, partially pregelatinized starch, pullulan, propylene glycol, starch syrup of reduced malt sugar powder, powdered cellulose, pectin, bentonite, sodium polyacrylate, polyoxyethylene alkyl ether, polyoxyethylene hardened castor oil, polyoxyethylene (105) polyoxypropylene (5) glycol, polyoxyethylene (160) polyoxypropylene (30) glycol, sodium polystyrene sulfonate, polysorbate, polyvinylacetal diethylaminoacetate, polyvinylpyrrolidone, polyethylene glycol (molecular weight: from 1500 to 6000), maltitol, maltose, D-mannitol, starch syrup, isopropyl myristate, anhydrous lactose, anhydrous dibasic calcium phosphate, an anhydrous dibasic calcium phosphate granulated product, magnesium aluminometasilicate, methylcellulose, cottonseed powder, cottonseed oil, haze wax, aluminum monostearate, glyceryl monostearate, sorbitan monostearate, pharmaceutical carbon, peanut oil, aluminum sulfate, calcium sulfate, grain corn starch, liquid paraffin, dl-malic acid, calcium monohydrogen phosphate, calcium hydrogen phosphate, a calcium hydrogen phosphate granulated product, sodium hydrogen phosphate, potassium dihydrogen phosphate, calcium dihydrogen phosphate and sodium dihydrogen phosphate.

Examples of the disintegrant include those classified as disintegrants in "Iyakuhin Tenkazai Jiten (Pharmaceutical Additive Dictionary)" (published by Yakuji Nippo Limited), such as celluloses such as croscarmellose sodium, carmellose, carmellosecalcium, carmellose sodium and low substitution degree hydroxypropyl cellulose, starches such as sodium carboxymethyl starch, hydroxypropyl starch, rice starch, wheat starch, corn starch, potato starch and partially pregelatinized starch, and synthetic polymers such as crospovidone and a crospovidone copolymer.

Examples of the binder include those classified as binders in "Iyakuhin Tenkazai Jiten (Pharmaceutical Additive Dictionary)" (published by Yakuji Nippo Limited), such as sugars such as white soft sugar, glucose, lactose and fructose, sugar alcohols such as mannitol, xylitol, maltitol, erythritol and sorbitol, water-soluble polysaccharides such as gelatine, pullulan, carrageenan, locust bean gum, agar, glucomannan, xanthan gum, tamarind gum, pectin, sodium alginate and gum arabic, celluloses such as crystalline cellulose, powdered cellulose, hydroxypropyl cellulose and methylcellulose, starches such as corn starch, potato starch, pregelatinized starch and starch paste, synthetic polymers such as polyvinylpyrrolidone, a carboxyvinyl polymer and polyvinyl alcohol, and inorganic compounds such as calcium hydrogen phosphate, calcium carbonate, synthetic hydrotalcite and magnesium aluminosilicate.

Examples of the fluidizing agent include those classified as fluidizing agents in "Iyakuhin Tenkazai Jiten (Pharmaceutical Additive Dictionary)" (published by Yakuji Nippo Limited), such as silicon compounds such as hydrous silicon dioxide and light anhydrous silicic acid, wet silicas such as sodium silicate, calcium silicate, and sodium stearyl fumarate (trade name: "PRUV" produced by JRS PHARMA).

Examples of the lubricant include those classified as lubricants in "Iyakuhin Tenkazai Jiten (Pharmaceutical Additive Dictionary)" (published by Yakuji Nippo Limited), such as magnesium stearate, calcium stearate, stearic acid, sucrose fatty acid ester, talc, fujicalin, and sodium stearyl fumarate (trade name: "PRUV" produced by JRS PHARMA).

Examples of the corrigent include those classified as corrigents in "Iyakuhin Tenkazai Jiten (Pharmaceutical Additive Dictionary)" (published by Yakuji Nippo Limited), such as glutamic acid, fumaric acid, succinic acid, citric acid, sodium citrate, tartaric acid, malic acid, ascorbic acid, sodium chloride and 1-menthol.

Examples of the flavoring agent include those classified as flavors and flavoring agents in "Iyakuhin Tenkazai Jiten (Pharmaceutical Additive Dictionary)" (published by Yakuji Nippo Limited), such as orange, vanilla, strawberry, yogurt, menthol, oils such as fennel oil, cinnamon bark oil, spruce oil and peppermint oil, and green tea powder.

Examples of the colorant include those classified as colorants in "Iyakuhin Tenkazai Jiten (Pharmaceutical Additive Dictionary)" (published by Yakuji Nippo Limited), such as edible dyes such as Food Red No. 3, Food Yellow 5 and Food Blue 1, sodium copper chlorophyllin, titanium oxide, and riboflavin.

Examples of the sweetener include those classified as sweeteners in "Iyakuhin Tenkazai Jiten (Pharmaceutical Additive Dictionary)" (published by Yakuji Nippo Limited), such as aspartame, saccharin, dipotassium glycyrrhizinate, stevia, maltose, maltitol, starch syrup and powdered sweet hydrangea leaf.

The form of the molded article is not particularly limited, and, for example, when the molded article is used for a pharmaceutical product, examples of the form include solid formulations such as a tablet, a powder, a subtle granule, a granule and a pill.

Hereinafter, a tablet, which is a suitable specific example of the molded article of the present embodiment, will be described.

A mixture of the composite particle of the present embodiment, the active ingredient, and if necessary other additive(s) can be tableted to thereby provide a tablet. The composite particle of the present embodiment is excellent in compression moldability, and therefore a practical tablet is obtained at a relatively low compression pressure. The composite particle can be molded into a tablet at a low compression pressure, and therefore a void (water conduit) can be maintained within the tablet, and thus the tablet is suitable as an orally disintegrating tablet which should be rapidly disintegrated in the oral cavity. In addition, the composite particle of the present embodiment is suitable for a multilayer tablet and a dry-coated tablet, which are obtained by compression molding of several ingredients at one stage or multiple stages, thereby exerting the effects of imparting excellent hardness to the molded article, suppressing tableting failures, and suppressing interlayer peeling and cracking. Furthermore, the composite particle of the present embodiment itself is splittable, and therefore the resulting tablet can be easily splitted uniformly and is also suitable for a splittable tablet and the like.

Generally, a composite particle has a porous structure and is excellent in retaining not only a fine particle drug, but also a liquid ingredient such as a suspension drug and a solution ingredient, and thus the composite particle of the molded article of the present embodiment is also excellent in liquid ingredient retention property. Therefore, there is also the following effect: in layering or coating a tablet with a suspension or solution ingredient, an outerlayer such as a coating layer is prevented from being peeled off. Accordingly, the composite particle of the present embodiment is also suitable for a layered tablet and a tablet having a coating layer (a sugar-coated tablet, a tablet with a stacked ingredient such as calcium carbonate, and the like).

Hereinafter, the method of producing the molded article including the active ingredient and the composite particle of the present embodiment will be described. Herein, such a method is one example and the present invention is not intended to be limited to the following description.

Examples of the method of molding the molded article include a method including mixing the active ingredient and the composite particle of the present embodiment, and thereafter compression molding the mixture. In addition to the active ingredient, the additive(s) described above may be compounded as required. The order of addition is not particularly limited, and examples include the following molding methods.

1) A method including collectively mixing the active ingredient, the composite particle of the present embodiment, and, if necessary, additive(s), and compression molding the mixture.
2) A method including mixing the active ingredient and an additive such as a fluidizing agent or a lubricant, thereafter mixing the composite particle of the present invention, and, if necessary, additional additive(s) therewith, and thereafter compression molding the mixture.
3) A method including further adding a lubricant to the mixed powder for compression molding, obtained by 1) or 2), and compression molding the resultant.

The method of adding respective ingredients is not particularly limited, and any method commonly performed can be used. The ingredients may be continuously added or collectively loaded by using a small size suction transport apparatus, an air transport apparatus, a bucket conveyor, a pneumatic transport apparatus, a vacuum conveyer, a vibration type quantitative metering feeder, a spray, a funnel, or the like.

The mixing method is not particularly limited, and any method commonly performed can be employed. A vessel rotation type mixer such as a V-type, W-type, double cone type or container tack type mixer, a stirring type mixer such as a high speed stirring type, universal stirring type, ribbon type, pug type or Nauta-type mixer, a high speed fluid type mixer, a drum type mixer, or a fluidized bed type mixer may be used. Alternatively, a vessel shaking type mixer such as a shaker can also be used.

The compression molding method is not particularly limited, and any method commonly performed can be employed. A method where compression molding into a desired shape is performed by use of a mortar and a pestle, or a method where compression molding into a sheet shape is performed in advance and thereafter fracturing into a desired shape is performed may be adopted. As a compression molding machine, for example, a roller type pressing machine such as a hydrostatic pressing machine, a briquetting roller type pressing machine or a smoothing roller type pressing machine, or a compression machine such as a single-punch tableting machine or a rotary tableting machine can be used.

When an active ingredient hardly soluble or insoluble in water is used, the following compression molding methods can be employed.
A) A method including pulverizing the active ingredient, thereafter mixing the composite particle of the present embodiment and, if necessary, other ingredients, and compression molding the mixture.
B) A method including dissolving or dispersing the active ingredient in water, an organic solvent or a solubilizing agent, thereafter mixing the composite particle of the present embodiment, and, if necessary, other additive(s), and, if necessary, distilling off water or the organic solvent, and compression molding the resultant.

The composite particle of the present embodiment is particularly suitably subjected to compression molding according to method B) above. In method B), a step of dissolving or dispersing the active ingredient, which is hardly soluble or insoluble in water, is once performed, and therefore the active ingredient can be securely supported on the composite particle. Thus, the active ingredient can be prevented from being separated or leaked out during compression molding, thereby resulting in suppression of sticking.

The composite particle of the present embodiment is high in compression moldability and fluidity, and therefore can provide a tablet small in variation in the weight by compression molding even in method B) above.

Method B) above is more suitable in the case where the active ingredient is a drug for use in a pharmaceutical product and a liquid medium such as polyethylene glycol is used in combination as a dispersion medium. Use of polyethylene glycol or the like is for the purpose of covering the active ingredient with polyethylene glycol in blood when absorbed in the body to thereby maintain the drug efficacy of the active ingredient having the property of being easily metabolized in the liver.

In method B) above, it is effective to use in combination a water-soluble polymer and/or a surfactant as a solubilizing agent by dispersing in the medium.

In method B) above, the organic solvent is not particularly limited, and any organic solvent used in a pharmaceutical product can be used. Examples thereof include those classified as solvents in "Iyakuhin Tenkazai Jiten (Pharmaceutical Additive Dictionary)" (published by Yakuji Nippo Limited), such as alcohols such as methanol and ethanol, and ketones such as acetone, and these may be used in combinations of two or more thereof.

Examples of the water-soluble polymer as the solubilizing agent in method B) above include water-soluble polymers described in "Iyakuhin Tenkazai Jiten (Pharmaceutical Additive Dictionary)" (published by Yakuji Nippo Limited), such as hydroxypropyl cellulose, hydroxypropyl methylcellulose, polyacrylic acid, a carboxyvinyl polymer, polyethylene glycol, polyvinyl alcohol, polyvinylpyrrolidone, methylcellulose, ethyl cellulose, gum arabic and starch paste, and these may be used in combinations of two or more thereof.

Examples of oils and fats as the solubilizing agent include oils and fats described in "Iyakuhin Tenkazai Jiten (Pharmaceutical Additive Dictionary)" (published by Yakuji Nippo Limited), such as monoglyceride stearate, triglyceride stearate, sucrose stearic acid ester, paraffins such as liquid paraffin, carnauba wax, hardened oils such as hardened castor oil, castor oil, stearic acid, stearyl alcohol, and polyethylene glycol, and these may be used in combinations of two or more thereof.

Examples of the surfactant as the solubilizing agent include those classified as surfactants in "Iyakuhin Tenkazai Jiten (Pharmaceutical Additive Dictionary)" (published by Yakuji Nippo Limited), such as phospholipid, glycerin fatty acid ester, polyethylene glycol fatty acid ester, sorbitan fatty acid ester, polyoxyethylene hardened castor oil, polyoxyethylene cetyl ether, polyoxyethylene stearyl ether, polyoxyethylene nonyl phenyl ether, polyoxyethylene polyoxypropylene glycol, polyoxyethylene sorbitan monolaurate, polysorbate, sorbitan monooleate, glyceride monostearate, monooxyethylene sorbitan monopalmitate, monooxyethylene sorbitan monostearate, polyoxyethylene sorbitan monooleate, sorbitan monopalmitate and sodium lauryl sulfate, and these may be used in combinations of two or more thereof.

In method B) above, the dissolving or dispersing method is not particularly limited. Any dissolving or dispersing method commonly performed can be employed, and a stirring/mixing method using a portable mixer, a three-dimensional mixer, a side-wall mixer or the like of a one-direction rotation type, multi-axis rotation type, reciprocal inversion type, vertical movement type, rotation+vertical movement type or piping type stirring blade, a jet type stirring/mixing method using a line mixer or the like, an air blowing type stirring/mixing method, a mixing method using a high-shear homogenizer, a high-pressure homogenizer, an ultrasonic homogenizer or the like, or a vessel shaking type mixing method using a shaker may be used.

The composite particle of the present embodiment has a porous structure and the composite particle by itself is excellent in retention property of the active ingredient such as a drug, and therefore the particle supporting the active ingredient in the pores thereof may be used as a fine grain as it is, may be used a granule after being granulated, or may be used after being compression molded.

The method of supporting the active ingredient on the composite particle is not particularly limited, and any known method can be employed. Examples include the following methods.

i) In the case of a fine particulate active ingredient: a method including mixing the active ingredient and the composite particle of the present embodiment to thereby support the active ingredient in the pores of the composite particle.

ii) In the case of a powdered active ingredient: a method including mixing the active ingredient and the composite particle of the present embodiment at a high speed to thereby forcedly support the active ingredient on the composite particle.

iii) A method including forming the active ingredient into a solution or a dispersion liquid once, mixing the dispersion liquid and the composite particle of the present embodiment, supporting the active ingredient on the composite particle, and thereafter, if necessary, drying the resultant.

iv) In the case of a sublimable active ingredient: a method including mixing the active ingredient and the composite particle of the present embodiment, and heating and/or depressurizing the mixture to thereby allow the active ingredient to sublimate and adsorb into the pores of the composite particle.

v) A method including mixing the active ingredient and the composite particle of the present embodiment before or during heating, and heating and melting the mixture.

The above methods may be used in combinations of two or more thereof.

Since the composite particle of the present embodiment is excellent in retention properties of solid and liquid ingredients, it can be used not only in the form of compression molded tablet, but in the form of a granule or powder particularly for the purpose of improvements in fluidity, blocking resistance and aggregation resistance. The fine granule and the granule may be here further coated.

Even when, for example, any of dry granulation, wet granulation, heating granulation, spray drying and microencapsulation methods is used as the method of producing the granule and the powder, the same effect is achieved.

The composite particle of the present embodiment has proper water retention property and oil retention property, and therefore can also be used as not only an excipient but also a nuclear particle for layering and/or coating and has the effect of suppressing particle aggregation in a layering and/or coating step. The layering and/or coating method may be a dry method or a wet method.

Although details mainly with respect to a pharmaceutical product is described in the above, the composite particle of the present embodiment can be used also for foods such as confectionery, a health food, a texture-improving agent and a dietary fiber-reinforcing agent, cake makeup, a bath agent, an animal drug, a diagnostic agent, a pesticide, a fertilizer, a ceramic catalyst, and the like.

EXAMPLES

Hereinafter, the present invention will be described based on Examples. The present invention, however, is not intended to be limited to the description of these Examples.

Herein, measurement methods of respective physical properties in Examples and Comparative Examples are as follows.

(1) Average Width (μm) of Cellulose Particle

A cellulose primary particle was dried as required, and mounted on a sample stage where a carbon tape was put, then platinum palladium was vacuum deposited (the thickness of the deposited film was here 20 nm or less). The resultant was observed using JSM-5510LV (trade name) manufactured by JASCO Corporation at an accelerating voltage of 6 kV and at a magnification of 250 times, and a short diameter in the vicinity of the center of a long diameter of the cellulose particle was determined as a representative width. The width was measured with respect to representative three of the cellulose primary particles, and the average value was defined as the average width of the cellulose particle.

(2) Average Thickness (μm) of Cellulose Particle

A cellulose primary particle, was dried as required, and mounted on a sample stage where a carbon tape was put, then gold was vacuum deposited. Thereafter the cross section of the cellulose primary particle (cross section in parallel with a short diameter) was cut out by Ga ion beam by use of a focused ion beam processing apparatus (manufactured by Hitachi Ltd., FB-2100 (trade name)) and then observed at an accelerating voltage of 6 kV and at a magnification of 1500 times, and the value of a shorter diameter of the cross section of the cellulose particle was measured as the thickness. The thickness was measured with respect to representative three of the cellulose primary particles, and the average value was defined as the average thickness of the cellulose particle.

(3) Average Volume Particle Sizes (μm) of Cellulose Particle and Inorganic Compound Particle The average volume particle sizes were each represented as the 50% cumulative volume particle size obtained by subjecting a dispersion liquid, in which a cellulose particle or an inorganic compound particle was dispersed in water, to a measurement using a laser diffraction particle size distribution analyzer (manufactured by HORIBA, Ltd., LA-910 (trade name)) in selected measurement modes of Stirring 4 and Circulation 5 in conditions of a transmittance of around 85%, an ultrasonic treatment time of 1 minute and a refractive index of 1.20.

Herein, the measurement value, and the particle size distribution of a dry particle obtained by the following Ro-tap system do not necessarily correlate to each other because of being completely different from each other in measurement principle. The average volume particle size measured by laser diffraction is determined from the volume frequency depending on the long diameter of a fabric particle, and on the other hand, the weight average particle size obtained by the Ro-tap system depends on the short diameter of a fabric particle because the resulting powder is shaken and fractioned on a sieve. Accordingly, the value depending on the long diameter of a fabric particle, obtained by the laser diffraction system, may be larger than that depending on the short diameter of a fabric particle, obtained by the Ro-tap system.

(4) Weight Average Particle Size (μm) of Composite Particle

The weight average particle size of a powder sample (dried composite particle) was represented as the 50% cumulative weight particle size obtained by sieving 10 g of the sample for 10 minutes by use of a Ro-tap type sieve shaker (manufactured by Heiko Seisakusho Ltd., trade name: "Sieve Shaker Model A") with a JIS standard sieve (Z8801-1987) to thereby measure the particle size distribution. The sizes (apertures) of the sieve used in measurement of the particle size distribution were 300 μm, 212 μm, 177 μm, 150 μm, 106 μm, 75 μm and 38 μm.

Particle sizes of +75 μm, from 75 to 32 μm, −32 μm were determined by sieving 10 g of the sample for 10 minutes by use of Air Jet Sieve (manufactured by Alpine) with two JIS standard sieves (Z8801-1987) having sizes (apertures) of 75 μm and 32 μm.

(5) Repose Angle (°) of Composite Particle

A sample was continuously deposited little by little (approximately 3 g/min) on a measurement portion with an electromagnetic feeder (Model MF-1/Tsutsui Scientific Instruments Co., Ltd.) by use of a Sugihara-type repose angle measurement instrument (slit size: 10 mm in depth×50 mm in width×140 mm in height, a protractor was disposed at a position of 50 mm in width), to thereby produce an inclined plane. As soon as an excess of the sample started to drop and the inclined plane was almost linear, the feeder was turned off, and the angle of the inclined plane measured by the protractor disposed was defined as the repose angle.

(6) Compression Molding Method of Sample

Each sample (0.5 g) was weighed, placed in a mortar (manufactured by Kikusui Seisakusho Ltd., material SUS2,3 was used), compressed by a pestle having a circular surface having a diameter of 1.1 cm (manufactured by Kikusui Seisakusho Ltd., material SUS2,3 was used) until the pressure was reached 10 MPa (manufactured by Aikou Engineering Co., Ltd., trade name: "P CM-1A", compression rate: 1 cm/min), and retained at a target pressure for 10 seconds, thereby producing a cylindrical molded article.

(7) Hardness (N) (AT Hardness) of Molded Article (Tablet)

A load was applied in the diameter direction of a cylindrical molded article or tablet by use of a Schleuniger hardness tester (manufactured by Freund Corporation, trade name: "Model 8M"), and a load at which the cylindrical molded article or tablet was broken was measured. The hardness was represented as the average value resulting from ten samples.

(8) Apparent Specific Volume (cm$^3$/g) of Composite Particle

A 25-cm$^3$ container was disposed in a Scott Volumeter (manufactured by VWR SCIENTIFIC, Model S64985). Next, each sample was charged at a rate of from 10 to 20 g/min by use of an electromagnetic feeder (Model MF-1/Tsutsui Scientific Instruments Co., Ltd.). When the sample overflowed from the container disposed, the container was taken out, an excessive content was leveled off, and the sample mass was measured. The value (cm$^3$/g) obtained by dividing the container volume (25 cm$^3$) by the sample mass was defined as the apparent specific volume. Such measurement was performed twice, and the average value was determined.

(9) Occurrence Rate of Sticking (%)

Fifty tablets were visually examined, and the number of tablet(s) having defects such as peeling on the surface(s) thereof was counted. The proportion of the number of tablet(s) on which sticking was observed was defined as the occurrence rate of sticking (%).

(10) Weight CV Value of Molded Article (Tablet)

Ten tablets obtained by tableting were arbitrarily sampled and subjected to mass measurement, and the weight CV value was determined from the average value and the standard deviation of the measurement values according to the expression: Weight CV value=(Standard deviation/Average value)×100 [%].

A large weight CV value means a large variation in mass and a large variation in content of the active ingredient, and leads to a reduction in production yield. Specifically, a case where the weight CV value is more than 1.0% is problematic in practical use.

(11) Taking of Scanning Electron Micrograph (Hereinafter, Abbreviated as "SEM") of Composite Particle Observation was made using an electron micrograph (manufactured by JEOL Ltd., Model JSM-551OLV). A sample was mounted on a sample moving stage, and the surface of the sample was evenly thinly covered with a metal particle by a gold vapor deposition method (AUTO FINE COATER, manufactured by JEOL Ltd., Model JFC-1600). Thereafter, the resultant was mounted in a sample chamber, the sample chamber was evacuated and the sample position was irradiated with electron beam, and an enlarged image of a portion to be observed was output and taken.

(12) Average Polymerization Degree of Cellulose

The average polymerization degree of the cellulose was measured by a copper ethylenediamine solution viscosity method described in the identification test (3) of crystalline cellulose in Japanese Pharmacopeia, Fourteenth Edition.

(13) L/D of Cellulose Particle Dispersed in Water

The average L/D of the cellulose particle dispersed in water was measured as follows. A JIS standard sieve (Z8801-1987) was used to allow a dispersion liquid of cellulose in water to pass therethrough, an optical microscope image of a particle passing through a 75 μm sieve and remaining in a 38 μm sieve was subjected to image analysis processing (manufactured by Inter Quest Co., Ltd., apparatus: Hyper 700, software: Imagehyper), and the ratio of the long side to the short side (long side/short side) of the rectangle having the smallest area among rectangles circumscribed on the particle was defined as L/D of the particle. The average value resulting from at least 100 particles was used as the average L/D of the particle.

Example 1

A pulp (the average width and the average thickness of a cellulose primary particle were about 19 μm and about 3 μm, respectively) obtained by subjecting a broad leaf tree to a known pulping treatment and a bleaching treatment was chipped, and 4.5 kg of the chipped pulp and 30 L of a 0.20% aqueous hydrochloric acid solution were placed in a low speed stirrer (manufactured by Ikebukuro Horo Kogyo Co., Ltd., trade name: 30LGL reactor) and subjected to hydrolysis at 120° C. for 1 hour with stirring, thereby providing a Wet cake of a cellulose particle as an acid-insoluble residue. The average volume particle size of the resulting cellulose particle was measured by a laser diffraction/scattering particle size distribution analyzer (manufactured by HORIBA, Ltd., trade name: "LA-910") at a refractive index of 1.20, and was found to be 67 μm.

Pure water was loaded into a plastic bucket, the Wet cake was added and mixed with stirring by 3-1 motor, hydroxypropyl cellulose (produced by Nippon Soda Co., Ltd., trade name: Celny (registered trademark)) was then added, and calcium silicate (produced by Priti Industries, trade name: CALCIUM CILICATE) was then added and mixed to provide a dispersion liquid. The mass ratio of cellulose/calcium silicate/hydroxypropyl cellulose was 60/30/10 (on a solid basis), and the total solid concentration of the dispersion liquid was about 14.0% by mass.

The resulting dispersion liquid was spray dried (the supply speed of the dispersion liquid: 6 kg/hr, the inlet temperature thereof: from 180 to 220° C., the outlet temperature thereof: from 70 to 95° C., the number of atomizer rotations: 30000 rpm), to provide composite particle A. Various physical properties of composite particle A are shown in Table-1.

A SEM photograph of composite particle A is illustrated in FIG. 1. It can be confirmed, with respect to composite particle A, from FIG. 1 that the cellulose, the inorganic compound and the hydroxypropyl cellulose primary particle are formed into a composite to form an aggregate (composite particle) having a void. The void enables a molded article high in liquid retention rate and a molded article with high hardness can be formed. For comparison, a SEM photograph of a simple mixture of powders of the cellulose, the inorganic compound and the hydroxypropyl cellulose is illustrated in FIG. 2. In such a mixture, the cellulose, the inorganic compound and the hydroxypropyl cellulose primary particle are separately present and do not form any aggregate.

Example 2

Pure water was loaded into a plastic bucket, the Wet cake obtained in Example 1 was added and mixed with stirring by 3-1 motor, hydroxypropyl cellulose (produced by Nippon Soda Co., Ltd., trade name: Celny (registered trademark)) was then added, and calcium silicate (produced by Priti Industries, trade name: CALCIUM CILICATE) was then added and mixed to provide a dispersion liquid. The mass ratio of cellulose/calcium silicate/hydroxypropyl cellulose was 65/30/5 (on a solid basis), and the total solid concentration of the dispersion liquid was about 14.1% by mass.

The resulting dispersion liquid was spray dried (the supply speed of the dispersion liquid: 6 kg/hr, the inlet temperature thereof: from 180 to 220° C., the outlet temperature thereof: from 70 to 95° C., the number of atomizer rotations: 30000 rpm), to provide composite particle B. Various physical properties of composite particle B are shown in Table-1.

Example 3

Pure water was loaded into a plastic bucket, the Wet cake obtained in Example 1 was added and mixed with stirring by 3-1 motor, hydroxypropyl cellulose (produced by Nippon Soda Co., Ltd., trade name: Celny (registered trademark)) was then added, and calcium silicate (produced by Priti Industries, trade name: CALCIUM CILICATE) was then added and mixed to provide a dispersion liquid. The mass ratio of cellulose/calcium silicate/hydroxypropyl cellulose was 65/30/5 (on a solid basis), and the total solid concentration of the dispersion liquid was about 16.5% by mass.

The resulting dispersion liquid was spray dried (the supply speed of the dispersion liquid: 6 kg/hr, the inlet temperature thereof: from 180 to 220° C., the outlet temperature thereof: from 70 to 95° C., the number of atomizer rotations: 30000 rpm), to provide composite particle C. Various physical properties of composite particle C are shown in Table-1.

Example 4

Pure water was loaded into a plastic bucket, the Wet cake obtained in Example 1 was added and mixed with stirring by 3-1 motor, hydroxypropyl cellulose (produced by Nippon Soda Co., Ltd., trade name: Celny (registered trademark)) was then added, and calcium silicate (produced by Priti Industries, trade name: CALCIUM CILICATE) was then added and mixed to provide a dispersion liquid. The mass ratio of cellulose/calcium silicate/hydroxypropyl cellulose was 65/30/5 (on a solid basis), and the total solid concentration of the dispersion liquid was about 17.6% by mass.

The resulting dispersion liquid was spray dried (the supply speed of the dispersion liquid: 6 kg/hr, the inlet temperature thereof: from 180 to 220° C., the outlet temperature thereof: from 70 to 95° C., the number of atomizer rotations: 30000 rpm), to provide composite particle D. Various physical properties of composite particle D are shown in Table-1.

Example 5

A pulp (the average width and the average thickness of a cellulose primary particle were about 19 μm and about 3 μm, respectively) obtained by subjecting a broad leaf tree to a known pulping treatment and a bleaching treatment was chipped, and 4.5 kg of the chipped pulp and 30 L of a 0.15% aqueous hydrochloric acid solution were placed in a low speed stirrer (manufactured by Ikebukuro Horo Kogyo Co., Ltd., trade name: 30LGL reactor) and subjected to hydrolysis at 120° C. for 1 hour with stirring, thereby providing a Wet cake of a cellulose particle. The average volume particle size of the resulting cellulose particle was measured by a laser diffraction/scattering particle size distribution analyzer (manufactured by HORIBA, Ltd., trade name: "LA-910") at a refractive index of 1.20, and was found to be 67 μm.

Pure water was loaded into a plastic bucket, the Wet cake was added and mixed with stirring by 3-1 motor, and the resultant was spray dried (the supply speed of the dispersion liquid: 6 kg/hr, the inlet temperature thereof: from 180 to 220° C., the outlet temperature thereof: from 70 to 95° C., the number of atomizer rotations: 30000 rpm), to provide a cellulose particle.

Pure water was loaded into a plastic bucket, the cellulose particle was added and mixed with stirring by 3-1 motor, hydroxypropyl cellulose (produced by Nippon Soda Co., Ltd., trade name: Celny (registered trademark)) was then added, and calcium silicate (produced by Priti Industries, trade name: CALCIUM CILICATE) was then added and mixed. The mass ratio of cellulose/calcium silicate/hydroxypropyl cellulose was 65/30/5 (on a solid basis), and the total solid concentration of the dispersion liquid was about 19.6% by mass.

The resulting dispersion liquid was spray dried (the supply speed of the dispersion liquid: 6 kg/hr, the inlet temperature thereof: from 180 to 220° C., the outlet temperature thereof: from 70 to 95° C., the number of atomizer rotations: 30000 rpm), to provide composite particle E. Various physical properties of composite particle E are shown in Table-1.

Example 6

Pure water was loaded into a plastic bucket, the cellulose particle obtained in Example 5 was added and mixed with stirring by 3-1 motor, Klucel™ (trade name) (produced by Ashland Inc.) was then added, and calcium silicate (produced by Priti Industries, trade name: CALCIUM CILICATE) was then added and mixed. The mass ratio of cellulose/calcium silicate/hydroxypropyl cellulose was 65/30/5 (on a solid basis), and the total solid concentration of the dispersion liquid was about 18.5% by mass.

The resulting dispersion liquid was spray dried (the supply speed of the dispersion liquid: 6 kg/hr, the inlet temperature thereof: from 180 to 220° C., the outlet temperature thereof: from 70 to 95° C., the number of atomizer rotations: 30000 rpm), to provide composite particle F. Various physical properties of composite particle F are shown in Table-1.

Example 7

Pure water was loaded into a plastic bucket, the cellulose particle obtained in Example 5 was added and mixed with stirring by 3-1 motor, Klucel™ (trade name) (produced by Ashland Inc.) was then added, and calcium silicate (produced by Priti Industries, trade name: CALCIUM CILICATE) was then added and mixed. The mass ratio of cellulose/calcium silicate/hydroxypropyl cellulose was 65/30/5 (on a solid basis), and the total solid concentration of the dispersion liquid was about 18.5% by mass.

The resulting dispersion liquid was shelf dried (dropped on aluminum foil drop by drop by a dropper, and dried at a temperature of 105° C. for 3 hours), to provide composite particle G. Various physical properties of composite particle G are shown in Table-1.

Comparative Example 1

Pure water was loaded into a plastic bucket, the Wet cake obtained in Example 1 was added and mixed with stirring by 3-1 motor, hydroxypropyl cellulose (produced by Nippon Soda Co., Ltd., trade name: Celny (registered trademark)) was then added, and calcium silicate (produced by Priti Industries, trade name: CALCIUM CILICATE) was then added and mixed. The mass ratio of cellulose/calcium silicate/hydroxypropyl cellulose was 65/32/3 (on a solid basis), and the total solid concentration of the dispersion liquid was about 14.0% by mass.

The resulting dispersion liquid was spray dried (the supply speed of the dispersion liquid: 6 kg/hr, the inlet temperature thereof: from 180 to 220° C., the outlet temperature thereof: from 70 to 95° C., the number of atomizer rotations: 30000 rpm), to provide composite particle G. Various physical properties of composite particle H are shown in Table-1.

Comparative Example 2

Pure water was loaded into a plastic bucket, the Wet cake obtained in Example 1 was added and mixed with stirring by 3-1 motor, and calcium silicate (produced by Priti Industries, trade name: CALCIUM CILICATE) was then added and mixed. The mass of cellulose/calcium silicate was 65/35 (on a solid basis), and the total solid concentration of the dispersion liquid was about 14.3% by mass.

The resulting dispersion liquid was spray dried (the supply speed of the dispersion liquid: 6 kg/hr, the inlet temperature thereof: from 180 to 220° C., the outlet temperature thereof: from 70 to 95° C., the number of atomizer rotations: 30000 rpm), to provide composite particle H. Various physical properties of composite particle I are shown in Table-1.

Comparative Example 3

Pure water was loaded into a plastic bucket, the Wet cake obtained in Example 5 was added and mixed with stirring by 3-1 motor, hydroxypropyl methylcellulose (produced by Shin-Etsu Chemical Co., Ltd., trade name: TC-5R) was then added, and calcium silicate (produced by Priti Industries, trade name: CALCIUM CILICATE) was then added and mixed. The mass ratio of cellulose/calcium silicate/hydroxypropyl methylcellulose was 60/30/10 (on a solid basis), and the total solid concentration of the dispersion liquid was about 16.3% by mass.

The resulting dispersion liquid was spray dried (the supply speed of the dispersion liquid: 6 kg/hr, the inlet temperature thereof: from 180 to 220° C., the outlet temperature thereof: from 70 to 95° C., the number of atomizer rotations: 30000 rpm), to provide composite particle I. Various physical properties of composite particle J are shown in Table-1.

Comparative Example 4

Pure water was loaded into a plastic bucket, the Wet cake obtained in Example 5 was added and mixed with stirring by 3-1 motor, starch (produced by Matsutani Chemical Industry Co., Ltd., trade name: Matsunorin M) was then added, and calcium silicate (produced by Priti Industries, trade name: CALCIUM CILICATE) was then added and mixed. The mass ratio of cellulose/calcium silicate/starch was 60/30/10 (on a solid basis), and the total solid concentration of the dispersion liquid was about 16.3% by mass.

The resulting dispersion liquid was spray dried (the supply speed of the dispersion liquid: 6 kg/hr, the inlet temperature thereof: from 180 to 220° C., the outlet temperature thereof: from 70 to 95° C., the number of atomizer rotations: 30000 rpm), to provide composite particle J. Various physical properties of composite particle K are shown in Table-1.

Comparative Example 5

A pulp (the average width and the average thickness of a cellulose primary particle were about 19 μm and about 3 μm, respectively) obtained by subjecting a broad leaf tree to a known pulping treatment and a bleaching treatment was chipped, and 4.5 kg of the chipped pulp and 30 L of a 0.2% aqueous hydrochloric acid solution were placed in a low speed stirrer (manufactured by Ikebukuro Horo Kogyo Co., Ltd., trade name: 30LGL reactor) and subjected to hydrolysis at 124° C. for 1 hour with stirring, thereby providing a Wet cake of a cellulose particle as an acid-insoluble residue. The average volume particle size of the resulting cellulose particle was measured by a laser diffraction/scattering particle size distribution analyzer (manufactured by HORIBA, Ltd., trade name: "LA-910") at a refractive index of 1.20, and was found to be 25 μm.

Pure water was loaded into a plastic bucket, starch (produced by Asahi Kasei Chemicals Corporation, trade name: "SWELSTAR" WB-1) was added and mixed with stirring by 3-1 motor, the Wet cake was then added and mixed, and calcium silicate (produced by Tokuyama Corporation, trade name: Florite R, average volume particle size 25 μm) was then added and mixed. The mass ratio of starch/cellulose/calcium silicate was 7/43/50 (on a solid basis), and the total solid concentration of the dispersion liquid was about 9.3% by mass (pH: 10.2).

The resulting dispersion liquid was spray dried (the supply speed of the dispersion liquid: 6 kg/hr, the inlet temperature thereof: from 180 to 220° C., the outlet temperature thereof: from 70 to 95° C., the number of atomizer rotations: 30000 rpm), to provide composite particle K.

Industries, trade name: CALCIUM CILICATE) was then added and mixed to provide a dispersion liquid. The mass ratio of cellulose/calcium silicate/hydroxypropyl cellulose was 55/30/15 (on a solid basis), and the total solid concentration of the dispersion liquid was about 14.3% by mass.

The resulting dispersion liquid was spray dried (the supply speed of the dispersion liquid: 6 kg/hr, the inlet temperature thereof: from 180 to 220° C., the outlet temperature thereof: from 70 to 95° C., the number of atomizer rotations: 30000 rpm), to provide composite particle N. Various physical properties of composite particle N are shown in Table-1.

TABLE 1

Physical properties of composite powder

| | | Composition of composite particle (parts by mass) | | | | | Total solid concentration of re-slurry [% by mass] | Physical properties of powder | | | | | |
|---|---|---|---|---|---|---|---|---|---|---|---|---|---|
| | | Cellulose | Inorganic compound | Hydroxypropyl cellulose | HPMC | Starch | | Apparent specific volume [cm³/g] | Repose angle [°] | Particle size D50 [μm] | +75 μm [%] | 75-32 μm [%] | -32 μm [%] |
| Example 1 | A | 60 | 30 | 10 | — | — | 14.0 | 6.13 | 41 | 43 | 9 | 45 | 46 |
| Example 2 | B | 65 | 30 | 5 | — | — | 14.1 | 6.17 | 41 | 40 | 5 | 36 | 59 |
| Example 3 | C | 65 | 30 | 5 | — | — | 16.5 | 6.96 | 43 | 38 | 3 | 31 | 66 |
| Example 4 | D | 65 | 30 | 5 | — | — | 17.6 | 5.88 | 42 | 42 | 8 | 38 | 54 |
| Example 5 | E | 65 | 30 | 5 | — | — | 19.6 | 5.71 | 42 | 33 | 2 | 8 | 90 |
| Example 6 | F | 65 | 30 | 5 | — | — | 18.5 | 5.84 | 42 | 30 | 1 | 17 | 82 |
| Example 7 | G | 65 | 30 | 5 | — | — | 18.5 | 5.92 | 41 | 35 | 3 | 10 | 87 |
| Comparative Example 1 | H | 65 | 32 | 3 | — | — | 14.0 | 6.13 | 43 | 39 | 3 | 32 | 65 |
| Comparative Example 2 | I | 65 | 35 | — | — | — | 14.3 | 5.88 | 45 | 39 | 8 | 27 | 65 |
| Comparative Example 3 | J | 60 | 30 | — | 10 | — | 16.7 | 5.20 | 36 | 53 | 22 | 56 | 22 |
| Comparative Example 4 | K | 60 | 30 | — | — | 10 | 14.9 | 4.01 | 38 | 55 | 25 | 57 | 18 |
| Comparative Example 5 | L | 43 | 50 | — | — | 7 | 9.3 | 9.00 | 43 | 47 | 15 | 60 | 26 |
| Comparative Example 6 | M | 65 | 30 | 5 | — | — | — | 9.80 | 60 | 25 | 1 | 12 | 87 |
| Comparative Example 7 | N | 55 | 30 | 15 | — | — | 14.3 | 6.00 | 41 | 42 | 7 | 47 | 46 |

Various physical properties of composite particle L are shown in Table-1.

Comparative Example 6

Mixture of cellulose, calcium silicate and hydroxypropyl methylcellulose (produced by Shin-Etsu Chemical Co., Ltd., trade name: TC-5R) where Ceolus KG-1000 (produced by Asahi Kasei Chemicals Corporation) was used as a crystalline cellulose and the mass ratio of cellulose/calcium silicate/hydroxypropyl methylcellulose was 65/30/5 was sufficiently mixed in a plastic bag for 3 minutes, to provide a mixed particle of cellulose/calcium silicate/hydroxypropyl cellulose. Various physical properties of mixed particle M are shown in Table-1.

Comparative Example 7

Pure water was loaded into a plastic bucket, the Wet cake obtained in Example 1 was added and mixed with stirring by 3-1 motor, hydroxypropyl cellulose (produced by Nippon Soda Co., Ltd., trade name: Celny (registered trademark)) was then added, and calcium silicate (produced by Priti Example 8

Each of composite particles A to L and N, and mixed particles M obtained in Examples 1 to 7 and Comparative Examples 1 to 7 was tableted by hydrostatic pressing (hereinafter, designated as "AT pressing") at a tablet weight of 500 mg and a tableting pressure of 1 KN with a pestle and a mortar for a flat tablet having a diameter of 11.5 mmφ. The hardness of the resulting tablet was shown in "Physical properties of tablet by hydrostatic pressing" in Table-2.

Thirty percent by mass of each of composite particles A to L and N or mixed particles M and 70% by mass of ascorbic acid (produced by BASF SE, product pulverized at 140000 rpm) were mixed, and tableted at a tablet weight of 500 mg and a tableting pressure of 1 KN with a pestle and a mortar for a flat tablet having a diameter of 11.5 mmφ. The hardness of the resulting tablet was shown in "Physical properties of tablet by hydrostatic pressing" in Table-2.

TABLE 2

Physical properties of tablet by hydrostatic pressing

| | | Composition of composite particle (parts by mass) | | | | | Total solid concentration of re-slurry [% by mass] | Physical properties of powder (hydrostatic pressing) | |
|---|---|---|---|---|---|---|---|---|---|
| | | Cellulose | Inorganic compound | Hydroxypropyl cellulose | HPMC | Starch | | Single, 1 kN, AT hardness [N] | Formulation, 7 kN, AT hardness |
| Example 1 | A | 60 | 30 | 10 | — | — | 14.0 | 76 | 102 |
| Example 2 | B | 65 | 30 | 5 | — | — | 14.1 | 99 | 121 |
| Example 3 | C | 65 | 30 | 5 | — | — | 16.5 | 73 | 100 |
| Example 4 | D | 65 | 30 | 5 | — | — | 17.6 | 72 | 89 |
| Example 5 | E | 65 | 30 | 5 | — | — | 19.6 | 72 | 115 |
| Example 6 | F | 65 | 30 | 5 | — | — | 18.5 | 63 | 97 |
| Example 7 | G | 65 | 30 | 5 | — | — | 18.5 | 70 | 100 |
| Comparative Example 1 | H | 65 | 32 | 3 | — | — | 14.0 | 74 | 98 |
| Comparative Example 2 | I | 65 | 35 | — | — | — | 14.3 | 75 | 86 |
| Comparative Example 3 | J | 60 | 30 | — | 10 | — | 16.7 | 75 | 78 |
| Comparative Example 4 | K | 60 | 30 | — | — | 10 | 14.9 | 57 | 81 |
| Comparative Example 5 | L | 43 | 50 | — | — | 7 | 9.3 | 220 | 151 |
| Comparative Example 6 | M | 65 | 30 | 5 | — | — | — | Too bulky to be packed in mortar | |
| Comparative Example 7 | N | 55 | 30 | 15 | — | — | 14.3 | 82 | 100 |

Example 9

In a polyethylene bag were mixed 70% by mass of ascorbic acid (produced by BASF SE, product pulverized at 140000 rpm), 2% by mass of croscarmellose sodium (produced by Nichirin Chemical Industries, Ltd., "Kiccolate" ND-2HS) and 28% by mass of composite particles A in Example 1 for 3 minutes. Next, 1.5% by mass of magnesium stearate (produced by Taihei Chemical Industrial Co., Ltd.) based on the total mass of the mixed powder was added and further slowly mixed for 30 seconds. The mixed powder was tableted by a rotary tableting machine (manufactured by Kikusui Seisakusho Ltd., LIBRA2) with a 12R pestle having a diameter of 0.8 cm at a number of turntable rotations of 30 rpm and a tableting pressure of 12 kN in a feeding condition with stirring, to produce a tablet whose mass was 180 mg. Physical properties of the tablet are shown in Table-3.

Example 10

A tablet was produced in the same manner as in Example 9 except that composite particles A in Example 1 were replaced with composite particles B in Example 2. Physical properties of the tablet are shown in Table-3.

Example 11

A tablet was produced in the same manner as in Example 9 except that composite particles A in Example 1 were replaced with composite particles E in Example 5. Physical properties of the tablet are shown in Table-3.

Example 12

A tablet was produced in the same manner as in Example 9 except that composite particles A in Example 1 were replaced with composite particles F in Example 6. Physical properties of the tablet are shown in Table-3.

Comparative Example 8

A tablet was produced in the same manner as in Example 9 except that composite particles A in Example 1 were replaced with composite particles H in Comparative Example 1. Physical properties of the tablet are shown in Table-3.

Comparative Example 9

A tablet was produced in the same manner as in Example 9 except that composite particles A in Example 1 were replaced with composite particles L in Comparative Example 5. Physical properties of the tablet are shown in Table-3.

Comparative Example 10

A tablet was produced in the same manner as in Example 9 except that composite particles A in Example 1 were replaced with composite particles N in Comparative Example 7. Physical properties of the tablet are shown in Table-3.

TABLE 3

Physical properties of molded article

| | | Composition of composite particle (parts by mass) | | | | Physical properties of tablet (tableting pressure: 12 kN) | | | | |
|---|---|---|---|---|---|---|---|---|---|---|
| | | Cellulose | Inorganic compound | Hydroxypropyl cellulose | HPMC | Starch | Weight CV [%] | Hardness [N] | Disintegration time (min) | Friability [%] | Rate of sticking (%) |
| Example 9 | A | 60 | 30 | 10 | — | — | 0.6 | 63 | 2.3 | 0.08 | 0 |
| Example 10 | B | 65 | 30 | 5 | — | — | 0.6 | 68 | 2.3 | 0.12 | 0 |
| Example 11 | E | 65 | 30 | 5 | — | — | 0.6 | 68 | 2.3 | 0.17 | 0 |
| Example 12 | F | 65 | 30 | 5 | — | — | 0.8 | 67 | 3.4 | 0.15 | 0 |
| Comparative Example 8 | H | 65 | 32 | 3 | — | — | 0.9 | 57 | 2.3 | 0.21 | 10 |
| Comparative Example 9 | L | 43 | 50 | — | — | 7 | 0.9 | 69 | 10.1 | 0.15 | 0 |
| Comparative Example 10 | N | 55 | 30 | 15 | — | — | 0.8 | 65 | 21.2 | 0.09 | 0 |

Example 13

Composite particles A obtained in Example 1 and ascorbic acid (produced by BASF SE, product pulverized at 140000 rpm) were mixed in equal amounts and stored in a constant temperature and constant humidity machine (conditions: 40° C. and 75% RH, open petri dish), and the whiteness of the resultant was observed on the next day. The results are shown in "Test results of reaction with ascorbic acid" in Table-4.

Example 14

Composite particles B obtained in Example 2 and ascorbic acid (produced by BASF SE, product pulverized at 140000 rpm) were mixed in equal amounts and stored in a constant temperature and constant humidity machine (conditions: 40° C. and 75% RH, open petri dish), and the whiteness of the resultant was observed on the next day. The results are shown in "Test results of reaction with ascorbic acid" in Table-4.

Comparative Example 11

Composite particles L obtained in Comparative Example 5 and ascorbic acid (produced by BASF SE, product pulverized at 140000 rpm) were mixed in equal amounts and stored in a constant temperature and constant humidity machine (conditions: 40° C. and 75% RH, open petri dish), and the whiteness of the resultant was observed by "Spectrophotometer type; SE2000 manufactured by NIPPON DENSHOKU" on the next day. The results are shown in "Test results of reaction with ascorbic acid" in Table-4.

Comparative Example 12

Composite particles N obtained in Comparative Example 7 and ascorbic acid (produced by BASF SE, product pulverized at 140000 rpm) were mixed in equal amounts and stored in a constant temperature and constant humidity machine (conditions: 40° C. and 75% RH, open petri dish), and the whiteness of the resultant was observed by "Spectrophotometer type; SE2000 manufactured by NIPPON DENSHOKU" on the next day. The results are shown in "Test results of reaction with ascorbic acid" in Table-4.

TABLE 4

Test results of reaction with ascorbic acid

| | | Whiteness [%] After one day |
|---|---|---|
| Example 13 | A | 88 |
| Example 14 | B | 86 |
| Comparative Example 11 | L | 78 |
| Comparative Example 12 | N | 79 |

A composite particles corresponding to that according to the present invention was used in each of Examples 9 to 12, to thereby provide a tablet having an operating hardness of 50 N or more and a weight CV value of 1.0% or less without causing any tableting failures (sticking).

On the other hand, Comparative Example 8 provided a tablet having a weight CV value of 1.0% or less, but caused a tableting failure (sticking), which is not suitable for a practical use. Comparative Example 9 provided a tablet having a weight CV value of 1.0% or less without causing any tableting failures (sticking), but exhibited a tablet disintegration time delayed about 4 times that in each of Examples 9, 10 and 11. Comparative Example 10 provided a tablet having a weight CV value of 1.0% or less without causing any tableting failures (sticking), but exhibited a tablet disintegration time delayed about 9 times that in each of Examples 9, 10 and 11.

It was confirmed from the results in Examples 13 and 14 and Comparative Examples 11 and 12 that, while composite particles A and B corresponding to that according to the present invention were reduced in whiteness to at most 88% and 86%, respectively, even when mixed with ascorbic acid, which is an acidic drug (active ingredient), composite particles L and N in Comparative Examples were reduced in whiteness to 78% and 79%, respectively, and turned yellow.

INDUSTRIAL APPLICABILITY

The composite particle of the present invention can be utilized as an excipient in preparation of a molded article, and in particular, can be suitably utilized as an excipient for a molded article including an active ingredient, since it is low in reactivity with an active ingredient.

Furthermore, the composite particle of the present invention hardly causes tableting failures such as sticking and capping to occur and hardly causes disintegration delay to occur even when molded together with a liquid ingredient, and thus can be suitably utilized as an excipient for a molded article including a liquid active ingredient.

The present application is based on Japanese Patent Application (Japanese Patent Application No. 2015-233138) filed with JPO on Nov. 30, 2015, the content of which is herein incorporated by reference.

The invention claimed is:

1. A composite particle comprising from 50 to 80 parts by mass of cellulose, from 10 to 40 parts by mass of an inorganic compound and from 4 to 11 parts by mass of hydroxypropyl cellulose based on 100 parts by mass of a total of contents of the cellulose, the inorganic compound, and the hydroxypropyl cellulose.

2. The composite particle according to claim 1, having an apparent specific volume of from 4 to 7 cm$^3$/g.

3. The composite particle according to claim 1, wherein the inorganic compound is at least one selected from the group consisting of hydrous silicon dioxide, light anhydrous silicic acid, synthetic aluminum silicate, aluminum magnesium hydroxide, magnesium aluminometasilicate, magnesium aluminosilicate, calcium silicate, amorphous silicon oxide hydrate, magnesium silicate, and hydrous magnesium silicate.

4. The composite particle according to claim 3, wherein the inorganic compound is calcium silicate.

5. The composite particle according to claim 1, wherein a 2% by mass aqueous solution of the hydroxypropyl cellulose has a viscosity at 20° C. of from 2 to 4000 mPa·s, and the hydroxypropyl cellulose has a molecular weight of from 40000 to 910000 Daltons.

6. The composite particle according to claim 1, having a weight average particle size of from 20 to 250 μm.

7. A molded article comprising the composite particle according to claim 1, and an active ingredient.

8. The molded article according to claim 7, wherein the active ingredient is an ingredient for a medicine or an ingredient for health food.

* * * * *